(12) United States Patent
Chance

(10) Patent No.: US 6,949,081 B1
(45) Date of Patent: Sep. 27, 2005

(54) SENSING AND INTERACTIVE DRUG DELIVERY

(75) Inventor: Britton Chance, Marathon, FL (US)

(73) Assignee: Non-Invasive Technology, Inc., Philadelphia, PA (US)

( * ) Notice: Subject to any disclaimer, the term of this patent is extended or adjusted under 35 U.S.C. 154(b) by 0 days.

(21) Appl. No.: 09/383,476

(22) Filed: Aug. 26, 1999

Related U.S. Application Data

(60) Provisional application No. 60/098,017, filed on Aug. 26, 1998.

(51) Int. Cl.[7] .................... A61M 31/00; A61M 37/00; A61N 1/30; F04B 53/00; A61B 5/00

(52) U.S. Cl. ................... 604/67; 604/66; 604/65; 604/21; 604/20; 604/131; 417/234; 600/300; 382/181

(58) Field of Search ................ 417/2; 600/322, 600/310, 300, 365, 519, 502–503; 374/123; 604/66–68, 64, 65, 20, 21, 131, 153; 128/204.2

(56) References Cited

U.S. PATENT DOCUMENTS

| | | | | |
|---|---|---|---|---|
| 3,449,121 A | * | 6/1969 | Astheimer et al. | 374/123 |
| 4,468,222 A | | 8/1984 | Lundquist | 604/153 |
| 4,474,570 A | | 10/1984 | Ariura et al. | 604/20 |
| 4,756,706 A | * | 7/1988 | Kerns et al. | 604/66 |

(Continued)

FOREIGN PATENT DOCUMENTS

| | | |
|---|---|---|
| WO | PCT/US93/05868 | 12/1993 |
| WO | WO 93/25145 | 12/1993 |
| WO | PCT/US94/03518 | 10/1994 |
| WO | WO 94/22361 | 10/1994 |
| WO | PCT/US94/07984 | 2/1995 |
| WO | WO 95/02987 | 2/1995 |
| WO | WO 97/20494 | 6/1997 |
| WO | PCT/US97/16309 | 3/1998 |
| WO | WO 98/10698 | 3/1998 |
| WO | WO 99/40840 | 8/1999 |
| WO | WO 99/40841 | 8/1999 |
| WO | WO 99/40842 | 8/1999 |

OTHER PUBLICATIONS

Morphopoulos et al, Tumour angiogenesis as a prognostic marker in infiltratin lobular carcinoma of the breat., Journal of pathology Sep. 1996 vol. 180 (1), pp. 44–49.*

Kato et al, A Clinicopathological study of angiogenesis in breast cancer, Nippon Geka Gakai Zasshi Oct. 1995 vol. 96 (10), pp. 709–719.*

Nippon Geka Bakkai Zasshi Oct. 1995; 96 (10): 709–17, a clinicopathological study of angiogenesis is breast cancer; Kato et al.*

Morphoulos et al, Tumor angiogenesis as a progonstic marker in infiltrating lobular carcinoma of the breast, Jouneal of Pathology Sep. 1996; 180(1): 44–9.*

(Continued)

Primary Examiner—Nicholas D. Lucchesi
Assistant Examiner—Roz Maiorino
(74) Attorney, Agent, or Firm—Fish & Richardson P.C.

(57) ABSTRACT

An interactive drug delivery system includes a drug delivery module, an optical probe, a local controller, and an optional central controller. The drug delivery module is constructed and arranged to deliver selected amounts of a drug into a subject. The optical probe is constructed and arranged to detect in a selected tissue region of the subject a manifestation caused by the delivered drug. The local controller is constructed and arranged to receive data from or transmit data to the optical probe and the drug delivery module. The local controller is arranged to correlate optical data, received from the optical probe, to selected data and provide signals to the drug delivery module for adjusting the amounts of the drug to be delivered into the subject.

16 Claims, 1 Drawing Sheet

U.S. PATENT DOCUMENTS

| | | | |
|---|---|---|---|
| 4,825,545 A | 5/1989 | Chase et al. .................. 30/153 |
| 4,942,883 A | 7/1990 | Newman .................... 128/798 |
| 4,972,331 A | 11/1990 | Chance ...................... 364/550 |
| 5,006,108 A | 4/1991 | LaPrade ..................... 604/20 |
| 5,013,293 A | 5/1991 | Sibalis ....................... 604/20 |
| 5,057,318 A | 10/1991 | Magruder et al. .......... 424/438 |
| 5,061,243 A | 10/1991 | Winchell et al. ............ 604/132 |
| 5,100,380 A | 3/1992 | Epstein et al. ............... 604/67 |
| 5,119,815 A | 6/1992 | Chance ...................... 128/633 |
| 5,122,974 A | 6/1992 | Chance ...................... 364/550 |
| 5,187,672 A | 2/1993 | Chance et al. ............. 364/550 |
| 5,338,157 A * | 8/1994 | Blomquist .................... 417/2 |
| 5,386,827 A * | 2/1995 | Chance et al. ............. 600/310 |
| 5,445,609 A | 8/1995 | Lattin et al. ................. 604/20 |
| 5,464,392 A | 11/1995 | Epstein et al. ............... 604/67 |
| 5,540,665 A | 7/1996 | Mercado et al. ........... 604/145 |
| 5,553,614 A | 9/1996 | Chance ...................... 128/633 |
| 5,564,417 A | 10/1996 | Chance ...................... 128/633 |
| 5,681,285 A | 10/1997 | Ford et al. .................. 604/151 |
| 5,697,896 A | 12/1997 | McNichols et al. ........... 604/20 |
| 5,733,876 A | 3/1998 | O'Reilly et al. .............. 514/12 |
| 5,762,918 A | 6/1998 | Thorpe .................... 424/78.17 |
| 5,782,755 A * | 7/1998 | Chance et al. ............. 600/322 |
| 5,785,688 A | 7/1998 | Joshi et al. ................. 604/141 |
| 5,807,263 A | 9/1998 | Chance ...................... 600/476 |
| 5,935,099 A * | 8/1999 | Peterson et al. ............. 604/65 |
| 2002/0017299 A1 * | 2/2002 | Hickle |

OTHER PUBLICATIONS

Slodkowska et al, Lung carcinoids, tumor angiogenesis in relation to clinciopathologic characteristics, Analytical Quantiom Cytolo histology 199 Jun.:21(3): 267–72.*

Nakopoulou et al, an immunohistochemcial analysis of angiogenesis in invasive breast cancer with correlations to cliciopathologic predictors, Anticancer Research Sep.–Oct. 1999:19(5C): 4547–53.*

* cited by examiner

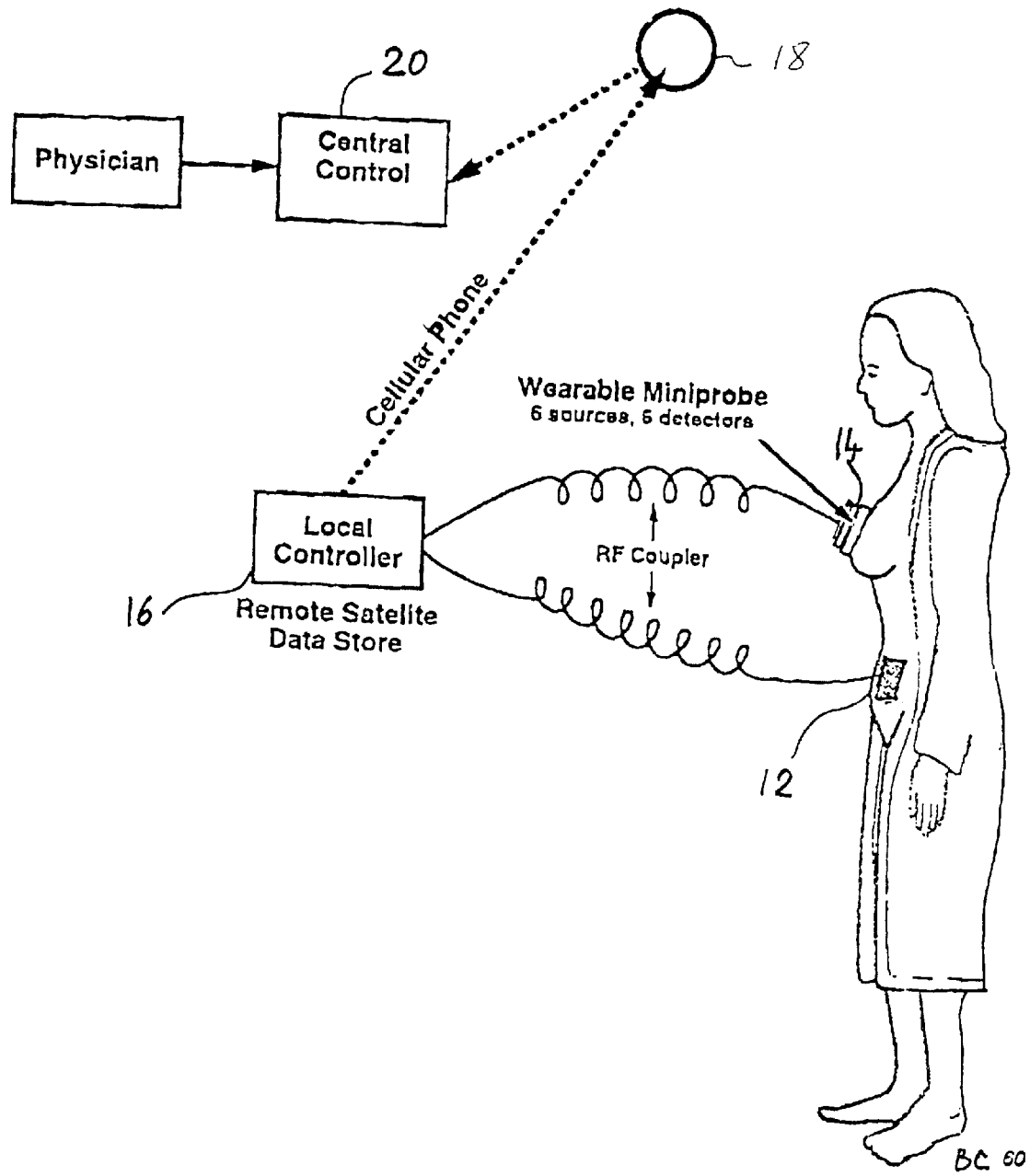

SENSING AND INTERACTIVE DRUG DELIVERY

This application claims priority from U.S. Provisional Application 60/098,017, filed on Aug. 26, 1998.

FIELD OF THE INVENTION

The present invention relates to interactive drug delivery systems and methods.

BACKGROUND

X-ray or γ-ray radiation, optical radiation, ultrasound waves, magnetic field have been used to examine and image biological tissue. X-rays or γ-rays propagate in the tissue on straight, ballistic lines, that is, their scattering is negligible. Thus, imaging is based on evaluation of the absorption levels of different tissue types. For example, in roentgenography the X-ray film contains darker and lighter spots. In more complicated systems, such as computerized tomography (CT), a cross-sectional picture of human organs is created by transmitting X-ray radiation through a section of the human body at different angles and by electronically detecting the variation in X-ray transmission. The detected intensity information is digitally stored in a computer that reconstructs the X-ray absorption of the tissue at a multiplicity of points located in one cross-sectional plane.

Near infra-red radiation (NIR) has been used to study non-invasively biological tissue including oxygen metabolism in the brain, finger, or ear lobe, for example. The use of visible, NIR and infra-red (IR) radiation for medical imaging may have several advantages. In the NIR or IR range the contrast factor between a tumor and a tissue is much larger than in the X-ray range. In addition, the visible to IR radiation is preferred over the X-ray radiation since it is non-ionizing and thus, potentially causes fewer side effects. However, the visible or IR radiation is strongly scattered and absorbed in biological tissue, and the migration path cannot be approximated by a straight line, making inapplicable certain aspects of cross-sectional imaging techniques.

Optical spectroscopy has been used to monitor and image tissue blood oxygenation and volume by measuring absorption of oxyhemoglobin and deoxyhemoglobin in the near infrared (NIR) wavelength region. Below 700 nm, light is strongly absorbed by hemoglobin, and above 900 nm, it is strongly absorbed by water. By making differential measurements at either side of the isosbestic point of oxy-hemoglobin and deoxy-hemoglobin absorbance (near 800 nm), it is possible to quantify the blood oxygenation and volume levels. Typically, these measurements are made at 750 nm and 830 nm.

NIR spectrometry adapted to the principles of computerized tomography has been used for in vivo imaging. This technique utilizes NIR radiation in an analogous way to the use of X-ray radiation in an X-ray CT. The X-ray source is replaced by several laser diodes emitting light in the NIR range. The NIR-CT uses a set of photodetectors that detect the light of the laser diodes transmitted through the imaged tissue. The detected data are manipulated by a computer similarly as the detected X-ray data would be in an X-ray CT. Different NIR-CT systems have recognized the scattering aspect of the non-ionizing radiation and have modified the X-ray CT algorithms accordingly.

The above-mentioned techniques have been used to detect a tissue tumor. The term "angiogenesis" refers to the generation of new blood vessels into a tissue or organ. Under normal physiological conditions humans or animals undergo angiogenesis only in very specific restricted situations. For example, angiogenesis is normally observed in wound healing, fetal and embryonal development and formation of the corpus luteum, endometrium and placenta.

Both controlled and uncontrolled angiogenesis are thought to proceed in a similar manner. Persistent, unregulated angiogenesis occurs in a multiplicity of disease states, tumor metastasis and abnormal growth by endothelial cells and supports the pathological damage seen in these conditions. The diverse pathological disease states in which unregulated angiogenesis is present have been grouped together as angiogenic dependent or angiogenic associated diseases. The hypothesis that tumor growth is angiogenesis dependent was first proposed in 1971. (Folkman J., Tumor Angiogenesis: Therapeutic Implications., N. Engl. Jour. Med. 285: 1182–1186, 1971) In its simplest terms it states: "Once tumor 'take' has occurred, every increase in tumor cell population must be preceded by an increase in new capillaries converging on the tumor." Tumor 'take' is understood to indicate a prevascular phase of tumor growth in which a population of tumor cells occupying a few cubic millimeters volume and not exceeding a few million cells, can survive on existing host microvessels. Expansion of tumor volume beyond this phase requires the induction of new capillary blood vessels. This explanation was directly or indirectly observed and documented in numerous publications.

After a tumor is detected by X-ray mammography, ultrasound, computerized tomography or MRI, the patient undergoes surgery, radiation therapy and/or drug therapy that frequently has negative effects on other organs and tissue of the patient. Furthermore, different patients respond differently to the drug therapy.

SUMMARY

In one aspect, an interactive drug delivery system includes a drug delivery module, an optical probe, and a local controller. The drug delivery module delivers selected amounts of a drug into a subject undergoing drug therapy while the optical probe detects the delivered drug, or a manifestation caused by the delivered drug, in a selected tissue region of the subject. The local) controller receives data from the optical probe and provides signals to the drug delivery module for adjusting the amounts of the drug to be delivered to the body.

In another aspect, an interactive drug delivery system includes a drug delivery module, an optical probe, a local controller, and a central controller. The drug delivery module delivers selected amounts of a drug into a subject undergoing drug therapy while the optical probe monitors a manifestation caused by the delivered drug in a selected tissue region of the subject. The local controller receives optical data from the optical probe and transmits data to the central controller. The central controller correlates the received data with control data and transmits data back to the local controller. The local controller provides signals to the drug delivery module for adjusting the amounts of the drug to be delivered to the body.

Preferred embodiments of these aspects include one or more of the following features:

The central controller includes a monitor for displaying the received data and suggested treatment data to a clinician. The central controller further includes an input device (e.g., a keyboard, a voice recognition system, a magnetic card reader) for entering control data to the central controller. The central controller further includes a data bank with various types of treatment data and optical data.

The interactive drug delivery system includes several drug delivery modules connected to the local controller. The interactive drug delivery system includes several additional probes, such as a temperature probe, a ultrasound probe, or an electrical probe including one or several electrodes that are implanted or attached to the skin. These probes are designed to monitor tissue properties, including the tissue metabolism, the heart rate, EKG, or the tissue temperature, and provide the measured data to the local controller.

The interactive drug delivery system enables continuous monitoring of a patient and adjusting interactively the drug delivery. Thus, the patient is able to move around the medical facility or leave the medical facility while undergoing drug therapy.

In another aspect, an interactive drug delivery method includes delivering by a drug delivery module selected amounts of a drug into a subject; optically detecting in a selected tissue region of said subject a manifestation caused by the delivered drug by an optical probe; and receiving data from or transmitting data to said optical probe and said drug delivery module by a local controller. The method also includes correlating data received from said optical probe to selected data stored in said local controller; and providing signals to said drug delivery module for adjusting the amounts of the drug to be delivered into said subject.

The interactive drug delivery method includes regulating the rate of the delivered drug based on signals from said local controller.

Other features and advantages will become apparent from the following detailed description and the accompanying FIG. 1, which shows an interactive drug delivery system using an optical probe.

DETAILED DESCRIPTION

With reference to FIG. 1, an interactive drug delivery system 10 includes a drug delivery module 12, an optical probe 14, a local controller 16, and a central controller 20. A human subject 11 (or an animal) undergoing a medical treatment wears local controller 16 interfaced with optical probe 14, drug delivery module 12, and optionally additional probes. Local controller 16 includes a processor, a memory and one or several interfaces including a wireless interface.

Drug delivery module 12 delivers selected amounts of a drug into the human body while optical probe 14 measures the concentration of the drug in a selected tissue region, or measures a selected response of a tissue region to the introduced drug, or measures changes in a selected tissue region, for example, a blood solute such as glucose, exogenous contrast agent or endogenous tissue pigment, and a tissue state such as blood volume or oxygenation of a tissue region, blood volume changes due to arterial pulse or the pulse rate).

Drug delivery module 12 and optical probe 14 provide data to local controller 16, which stores the data and provides the data to central controller 20 via a network 18, such as the cellular telephone network. The system 10 may include additional probes, such as a temperature probe, a ultrasound probe, an electrical probe including one or several electrodes that are implanted or attached to the skin. These probes are designed to monitor tissue properties, including metabolism, the heart rate or EKG, temperature, perspiration, and provide data to local controller 16. Interactive system 10 may also includes several additional drug delivery modules, responsive to local controller 16, for delivering several drugs according to a selected protocol.

Optical probe 14 is a non-invasive optical system that employs a CW spectrophotometer described in PCT application PCT/US95/15666, which is incorporated by reference. Alternatively, optical probe is a Time Resolved Spectroscopy (TRS) system as described in PCT applications PCT/US94/03518 or PCT/US94/07984 or U.S. Pat. No. 5,119,815 or U.S. Pat. No. 5,386,827, all of which are incorporated by reference. In another embodiment, optical probe 14 is a phase modulation system described in U.S. Pat. Nos. 4,972,331; 5,122,974; 5,187,672; 5,553,614 or 5,564,417, which are incorporated by reference. In another embodiment, optical probe 14 is a phased array, phase cancellation system described in PCT application PCT/US93/05868 or an amplitude cancellation system described in PCT application PCT/US95/15694, both of which are incorporated by reference as if fully set forth herein.

Optical probe 14 monitors directly a tissue constituent or a tissue region including an identified tumor during and after the drug delivery. Alternatively, optical probe 14 monitors a selected tissue organ to detect changes in the physiology of the tissue, or to monitor levels of a tissue solute attributable to the delivered drug. For example, optical probe 14 measures solute levels, such as glucose levels in the liver using the optical techniques described in the PCT Application PCT/US 95/15666. In this process, optical probe 14 evaluates changes in the scattering coefficient associated with the measured solute levels.

Local controller 16 receives optical data from optical probe 14. Furthermore, local controller 16 receives the temperature data, the EKG data, the heart rate data or the metabolism data. Local controller 16 compares the received data with stored data and stored instructions reflecting the expected treatment and the physiological changes caused by the delivered drug. After comparing the received data with the stored data, local controller 16 can provide control signals for adjusting or discontinuing the drug delivery performed by drug delivery module 12. Furthermore, local controller 16 can transmit the detected optical data and the stored data to central controller 20. Central controller 20 performs a data evaluation and provides the information to a physician. The physician evaluates the provided data and inputs dosing instructions into central controller 20, which in turn transmits the dosing instructions to local controller 16 for adjusting the drug delivery by drug delivery module 12. Local controller 16 further includes an input pad constructed and arranged for the human subject to input data including subjective condition of the human subject during the treatment. For example, the human subject can input information about fever, pain, nausea, vomiting, dizziness, or other symptoms.

Optical probe 14 is further constructed to measure the pulse rate of the subject during the drug delivery. Optical probe 14 detects increase in the pulse rate that may correspond to a sudden onset of tachycardia attributable, for example, to an anaphylactic reaction. The increase in the pulse rate may be accompanied with a temperature increase, corresponding to a drug related fever, or to an infection due to neutropenia or anemia caused by the delivered drug. The temperature probe measures the temperature of the subject and provides the temperature data automatically to local controller 16.

In another embodiment, as shown in FIG. 1, optical system 10 is used to monitor a breast tumor. Optical probe 14 detects a tumor as described in the PCT Application PCT/US 99/02953, entitled "Examination and Imaging of Breast Tissue", filed on Feb. 11, 1999 incorporated by reference herein. One or several drug delivery modules 12 deliver one or several drugs to the subject. For example, the drug treatment may include a combination regiment, such as CMF (Cyclophosphamide and Methotrexate and 5-Fluorouracil). Alternatively, drug delivery module 12 delivers a conjugated angiogenesis inhibitor for treatment of pathogenetic conditions, as described in U.S. Pat. No. 5,762, 918 entitled "Methods of Using Steroid-Polyanionic Polymer-Based Conjugated Targeted to Vascular Endothelical Cells" or angiogenesis inhibitor described in U.S. Pat. No. 5,733,876 entitled "Method of Inhibiting Angiogenesis", both of which are incorporated by reference. Optical probe 14 measures the local blood volume and oxygenation of the tissue region including, the detected tumor. Based on the measured blood volume and oxygenation, optical probe 14 monitors the growth and activity of the identified tumor. For example, optical probe 14 detects higher blood oxygenation that reflects a reduction in the tumor growth and activity. Based on this data, a local controller 16 provides signals to drug delivery module 12 for decreasing the drugs. Furthermore, upon detecting a sudden onset of tachycardia, local controller 16 may direct drug delivery module 12 to reduce or eliminate the delivery of the drug.

In another embodiment, system 10 is used to monitor the liver during a combination regiment for treatment of carcinoma. The CMF regiment causes optically detectable changes of one or several solutes in the liver. By measuring changes in the scattering coefficient at the measured wavelength, optical probe 14 detects changes in the solute concentration and provides the data to local controller 16, which adjusts the drug delivery. Alternatively, optical probe 14 is used to monitor drug delivery directly into the liver in treatment of hepatocellular carcinoma.

In another embodiment, interactive system 10 is used to monitor the drug delivery for treatment of diseases such as diabetes or cardiomyopathy. When treating diabetes, drug delivery module 12 includes an insulin pump, for providing controlled amount of insulin to a patient. Optical probe 14 is located on the abdominal region near the liver so that the detected optical radiation passes through the liver. Optical probe 14 detects the level of glucose as described in the PCT Application PCT/US95/15666, which is incorporated by reference as if fully provided herein. Upon detecting a low glucose level by optical probe 14, local controller 16 directs the insulin pump to reduce or discontinue the insulin delivery. The monitoring for hypoglycemia or hyperglycemia is also performed during the sleep of the patient to provide the data to local controller 16, which not only reduces the insulin delivery, but also sends a message to central controller 20 and a clinician receiving information at central controller 20. When treating cardiomyopathy, optical probe 14 measures the blood volume and saturation while drug delivery module 12 delivers the butamine, dopamine, or another drug.

Alternatively, optical probe 14 is TRS system, a phase-modulation system, a phased array, phase cancellation system, or an amplitude cancellation system for detecting fluorescent radiation. The principles of detecting fluorescent radiation were described by J. R. Lakowicz in "Principles of Fluorescence Spectroscopy," Plenum Press, N.Y., 1983. The delivered drug is "tagged" with an optically active contrast agent such as light absorbing contrast agent or a fluorescing contrast agent (e.g., ICG). Then, optical probe 14 uses a wavelength sensitive to the contrast agent, for example, a fluorescing contrast agent naturally occurring or delivered into the examined tissue.

For example, the delivered drug is "tagged" with a signal generator of high optical sensitivity and specificity, such as a molecular beacon. Molecular beacons are sense or antisense oligonucleotide probes that become fluorescent only in the presence of specific sequences of target nucleic acids. (described by Tyagi, S. and Kramer, F. R. "Molecular beacons: probes that fluoresce upon hybridization," Nature Biotech. 14, 303–8 (1996)). They consist of hairpin shaped molecules containing a loop of specific sequence nucleotide that is complementary to the target nucleic acid.

In the loop, the 3'- and 5'-ends of this loop contain 5–8 nucleotide strands that are complementary to each other; upon hybridization they form a 'stem' which holds the ends of the loop together. Attached to one of the stem oligonucleotides is a short linker with a fluorophore at its end; attached to the other stem is a linker connected to a quencher. The linkers are designed to juxtapose the fluorophore and quencher. Since fluorescence energy transfer (FET) depends on the inverse sixth power of the donor-acceptor distance, the molecular beacon is non-fluorescent when the stem segments are hybridized to each other; the transferred energy is dissipated as heat. When the loop hybridizes with the target nucleic acid, the hydrogen bonds between the complementary stem nucleotides are broken (since there are many more hydrogen bonds formed between the loop and the target), separating the fluorophore and quencher and producing detectable fluorescence. The length of the loop is chosen to optimize the approximation of the fluorophore and the quencher.

Molecular beacons have been used to detect specific amino acids in homogeneous solution. (see, Tyagi, S. and Kramer, F. R. "Molecular beacons: probes that fluoresce upon hybridization," Nature Biotech. 14, 303–8 (1996)). They are particularly useful for situations in which it is either not possible or desirable to isolate the probe-target hybrids, such as for real-time monitoring of polymerase chain reactions in sealed tubes or for detection of specific nucleic acids in cells. (see, Gao, W., Tyagi, S., Kramer, F. R. and Goldman, E. Messenger "RNA release from ribosomes during 5'-translational blockage by consecutive low-usage arginine but not leucine codons in *Eschericia coli,*" *Mol. Microbiol.* 25, 707–716 (1997); and Matsuo, T. "In situ visualization of mRNA for basic fibroblast growth factor in living cells," *Biochim. Biophys. Acta* 1379, 178–84 (1998)). Molecular beacons have been used to detect specific RNAs in hamster fibroblasts and human leukemia cells. (see, Sokol, D. L., Zhang, X., Lu, P. and Gewirtz, A. M. "Real time detection of DNA/RNA hybridization in living cells," *Proc. Natl. Acad. Sc. USA* 95, 11538–43 (1998)). Here, the molecular beacons are active in the near-infrared region and contain sense or antisence oligonucleotides targeted at specific mRNAs of solid tumor in vivo. This type of near infra-red fluorescent probe can be delivered by a variety of vehicles, such as apoE directed lipid vesicles for targeting tumor cells which overexpress low density lipoprotein (LDL) receptors, (see Rensen, P. C. N., Schiffelers, R. M., Versluis, J., Bijsterbosch, M. K., van Kuijk-Meuwissen, M. E. M. J. and van Berkel, T. J. C. "Human recombinant apolipoprotein E-enriched liposomes can mimic low density lipoproteins as carriers for the site-specific delivery of antitumor agents," *Molec. Pharmacol.* 52, 445–455 (1997)) such as B16 melanoma cells, (see de Smith, P. C. and van Berkel, T. J. C. "Prolonged serum half-life of antineoplastic drugs by incorporation into the low density lipoprotein," *Cancer Res.* 50, 7476082 (1990)) which will serve as a model tumor system for our study.

Optical probe 14 evaluates the tumor by evaluating the tissue and angiogenesis or by using enhanced fluorescent probe signaling cancer tissue based upon molecular abnormalities. A specific molecular beacon is used for detection of specific RNAs in specific tumors by targeting one or several enzymes. Several molecular beacons have been prepared with dyes detectable in the visible range of the optical spectrum, as described in Sokol, D. L., Zhang, X., Lu, P. And Gewirtz, A. M. "Real time detection of DNA/RNA hybridization in living cells," *Proc. Natl. Acad Sci. USA* 95, 11538–43 (1998).

A molecular beacon has its natural fluorescent quenched by hybridization in a target sequence. When duplex formation occurs, the fluorophores become separated and quenching is no longer possible. A dual wavelength system is used for absorption measurements and fluorescent measurements, as described above. The measurements are used to detect intrinsic and angiogenesis (or deoxygenation) signals from the tumor. The two wavelengths are encoded with different radio frequencies. Depending on the optical characteristic of optical module 14, ICG or Li-COR (manufactured by Li-Cor Company, Lincoln, Nebr.) is detected using the dual wavelength excitation measurement. For example, optical probe 14 is a dual wavelength phase cancellation system described in U.S. Pat. No. 5,807,263, which is incorporated by reference. The dual wavelength system uses laser diodes emitting light at 754 nm and 800 nm. The examined tissue is illuminated with either one of the wavelengths. These wavelengths excite fluorescent in ICG at 754 nm for low concentrations and at 800 nm for higher concentrations. The detected optical data is processed for phase detection or amplitude cancellation.

The dual wavelength system detects the sum of the detected optical signals at the two wavelengths to determine blood volume. The system also displays the difference of the two detected signals at the two wavelength to determine the oxygenation of hemoglobin, or may display the individual detected optical signals obtained from the absorption measurement. The detected 800 nm signal reflects the absorption of ICG and other agent and its derivatives. The fluorescent of the ICG and other agents at 830 nm is measured with the 754 nm and 800 nm excitation. This system employs optical primary and secondary filters as described in the above mentioned publication by J. R. Lakowicz.

Interactive system 10 is constructed for using various drug delivery modules. Drug delivery module 12 may be based on electrotransport, such as iontophoresis that involves electrically induced transport of charged ions, or electroosmosis that involves the movement of the liquid through a biological membrane such as the skin, or electroporosis that involves the transport of an agent through transiently existing pores formed in a biological membrane under the influence of the electric field. The electrotransport based module includes at least two electrodes in contact with a portion of the skin, mucous membrane, or another body surface, and at least one reservoir or source of the agent to be delivered to the body. The donor reservoir is connected to the donor electrode and positioned between the two electrodes to provide a renewable source of one or more agents or drugs. The drug delivery module also includes an electrical controller designed to regulate the rate of the drug delivery based on the signals from local controller 16.

Drug delivery module 12 may use different delivery devices described in U.S. Pat. No. 5,697,896, entitled "Electrotransport Delivery Device"; described in U.S. Pat. No. 5,445,609, entitled "Electrotransport Agent Delivery Device Having a Disposable Component and a Removable Liners"; described in U.S. Pat. No. 4,942,883, entitled "Drug Delivery Device"; described in U.S. Pat. No. 5,006,108, entitled "Apparatus for Iontophoretic Drug Delivery"; described in U.S. Pat. No. 4,474,570, entitled "Iontophoresis Device"; described in U.S. Pat. No. 5,013,293, entitled "Pulsating Transdermal Drug Delivery System"; described in U.S. Pat. No. 5,540,665, entitled "Gas Driven Dispensing Device and Gas Generating Engine Therefor"; or described in U.S. Pat. No. 5,057,318, entitled "Delivery System for Beneficial Agent Over a Broad Range of Rates," all of which are incorporated by reference.

Alternatively, drug delivery module 12 may use different devices described in U.S. Pat. No. 5,681,285, entitled "Infusion Pump with an Electronically Loadable Drug Library and a User Interface for Loading the Library"; described in U.S. Pat. No. 5,061,243, entitled "System and Apparatus for the Patient-Controlled Delivery of a Beneficial Agent, and set Therefor"; described in U.S. Pat. No. 5,464,392, entitled "Infusion System Having Plural Fluid Input Ports and at Least One Patient Output Port"; described in U.S. Pat. No. 4,468,222, entitled "Intravenous Liquid Pumping System and Method"; described in U.S. Pat. No. 5,785,688, entitled "Fluid Delivery apparatus and Method"; described in U.S. Pat. No. 4,828,545, entitled "Pressure Responsive Multiple Input Infusion system"; and also described in U.S. Pat. No. 5,100,380, entitled "Remotely Programmable Infusion System," all of which are incorporated by reference.

Additional embodiments are within the following claims.

What is claimed is:

1. An interactive drug delivery system comprising:
   a drug delivery module constructed and arranged to deliver selected amounts of a drug into a subject;
   an optical probe constructed and arranged to detect in vivo in a selected biological tissue region of said subject a manifestation caused by the delivered drug, said manifestation in said selected biological tissue region altering photon migration in said tissue due to said delivered drug; and
   a local controller constructed and arranged to receive data from or transmit data to said optical probe and said drug delivery module; said local controller being arranged to correlate optical data, related to said manifestation in said biological tissue region, received from said optical probe to selected data and provide signals to said drug delivery module for adjusting the amounts of the drug to be delivered into said subject.

2. The system of claim 1 further including a central controller remotely located from and in wireless communication with said local controller, central controller constructed and arranged to receive data from said local controller and provide to said local controller data for adjusting the amounts of said drug to be delivered into said subject.

3. The system of claim 1 or 2 further including a temperature probe coupled to said local controller.

4. The system of claim 3 wherein said temperature probe uses an infra-red beam to measure a local temperature of a tissue region.

5. The system of claim 1 or 2 further including an electrical probe coupled to said local controller.

6. The system of claim 1 or 2 wherein said optical probe is a TRS system.

7. The system of claim 1 or 2 wherein said optical probe is a phase modulation system.

8. The system of claim 1 or 2 wherein said optical probe is a phased array.

9. The system of claim 1 or 2 wherein said optical probe is a phase cancellation system.

10. The system of claim 1 or 2 wherein said optical probe is an amplitude cancellation system.

11. The system of claim 1 or 2 wherein said drug delivery module includes an electrical controller designed to regulate the rate of the delivered drug based on the signals from said local controller.

12. An interactive drug delivery method comprising:

delivering by a drug delivery module selected amounts of a drug into a subject;

optically detecting in vivo in a selected biological tissue region of said subject a manifestation caused by the delivered drug by an optical probe, said manifestation in said selected biological tissue region altering photon migration in said tissue due to said delivered drug;

receiving data from or transmitting data to said optical probe and said drug delivery module by a local controller;

correlating optical data, related to said manifestation in said biological tissue region, received from said optical probe to selected data stored in said local controller; and providing signals to said drug delivery module for adjusting the amounts of the drug to be delivered into said subject.

13. The interactive drug delivery method of claim 12 further including regulating the rate of the delivered drug based on signals from said local controller.

14. The interactive drug delivery method of claim 12 including measuring tissue temperature.

15. The interactive drug delivery method of claim 14 wherein said measuring temperature includes using an infrared beam for measuring a local temperature of a tissue region.

16. The interactive drug delivery method of claim 12 further including measuring electrical signals with an electrical probe.

* * * * *